(12) United States Patent
Suzuki

(10) Patent No.: US 8,130,383 B2
(45) Date of Patent: Mar. 6, 2012

(54) OPTICAL SIGNAL ANALYSIS APPARATUS AND OPTICAL SIGNAL ANALYSIS METHOD

(75) Inventor: Akemi Suzuki, Kokubunji (JP)

(73) Assignee: Olympus Corporation, Tokyo (JP)

( * ) Notice: Subject to any disclaimer, the term of this patent is extended or adjusted under 35 U.S.C. 154(b) by 537 days.

(21) Appl. No.: 12/055,763

(22) Filed: Mar. 26, 2008

(65) Prior Publication Data

US 2008/0306713 A1    Dec. 11, 2008

Related U.S. Application Data

(63) Continuation of application No. PCT/JP2006/319133, filed on Sep. 27, 2006.

(30) Foreign Application Priority Data

Sep. 27, 2005    (JP) ................................. 2005-279987

(51) Int. Cl.
*G01B 11/30*    (2006.01)

(52) U.S. Cl. .......... 356/602; 356/72; 356/317; 356/318; 356/417

(58) Field of Classification Search .................. 356/602, 356/72, 317–318, 417
See application file for complete search history.

(56) References Cited

U.S. PATENT DOCUMENTS

| | | | |
|---|---|---|---|
| 6,657,720 B1 * | 12/2003 | Kaselis .......................... | 356/317 |
| 6,980,294 B2 * | 12/2005 | Namba et al. ................. | 356/318 |
| 7,224,452 B2 * | 5/2007 | Hell ............................... | 356/317 |
| 7,355,701 B2 * | 4/2008 | Ishibashi ....................... | 356/300 |
| 7,602,479 B2 * | 10/2009 | Sawada et al. ................. | 356/72 |
| 7,719,679 B2 * | 5/2010 | Hell et al. ...................... | 356/318 |

FOREIGN PATENT DOCUMENTS

| | | |
|---|---|---|
| JP | 2004-108892 A | 4/2004 |
| JP | 2004-187581 | 7/2004 |
| JP | 2004-354348 A | 12/2004 |
| JP | 2004-361087 | 12/2004 |
| JP | 2005-17282 | 1/2005 |
| JP | 2006-78377 A | 3/2006 |
| JP | 2007-93277 A | 4/2007 |
| WO | WO 04/001402 A1 | 12/2003 |

OTHER PUBLICATIONS

Klaus Schaetzel, "New Concepts in Correlator Design", Inst. Phys. Conf. Ser. No. 77: Session 4, pp. 175-184, 1985.
Klaus Schaetzel e al., "Noise on Multiple-Tau Photon Correlation Data", SPIE Vo. 1430, Photo Correlation Spectroscopy: Multicomponent Systems, pp. 109-115, 1991.
Klaus Schaetzel et al., "Photon Correlation Measurements at Large Lag Times: Improving Statistical Accuracy", Journal of Modern Optics, Vo. 34, No. 4, pp. 711-718, 1988.

(Continued)

*Primary Examiner* — Gregory J Toatley
*Assistant Examiner* — Isiaka Akanbi
(74) *Attorney, Agent, or Firm* — Scully, Scott, Murphy & Presser, P.C.

(57) ABSTRACT

An optical signal analysis apparatus includes a photodetector and an analyzer. The photodetector is to detect light emitted from measurement points in a sample. The analyzer is to analyze a molecular interaction between two of the measurement points by using fluctuation signals corresponding to fluctuations of the light from the measurement points that are detected by the photodetector.

28 Claims, 13 Drawing Sheets

OTHER PUBLICATIONS

Yoshiaki Horikawa, Photon Counting Distribution Statistical Analysis for Single Fluorescence Molecules—For Studying Biomolecular Interactions, Journal of the Spectroscopical Society of Japan, vol. 53, No. 3, 1580-164, 2004.

Kazuhiko Mase et al., "Study of Ion Desorption Induced by Core-Electron Excitations of Molecules on Surface by Using Electron Ion Coincidence Spectroscopy", Journal of Japanese Society for Synchrotron Radiation Research, vol. 10, No. 4, pp. 375-391, 1997.

Petra Schwille et al., Dual-color fluorescence cross-correlation spectroscopy for multicomponent diffusional analysis in solution, Biophysical Journal, 1997, vol. 72 No. 4, pp. 1878-1886.

Kristen Bacia et al., A dynamic view of cellular processes by in vivo fluorescence auto- and cross-correlation spectroscopy, Methods, 2003, vol. 29 No. 1, pp. 74-85.

Japanese Official Action dated Jan. 18, 2011 together with English language translation.

* cited by examiner

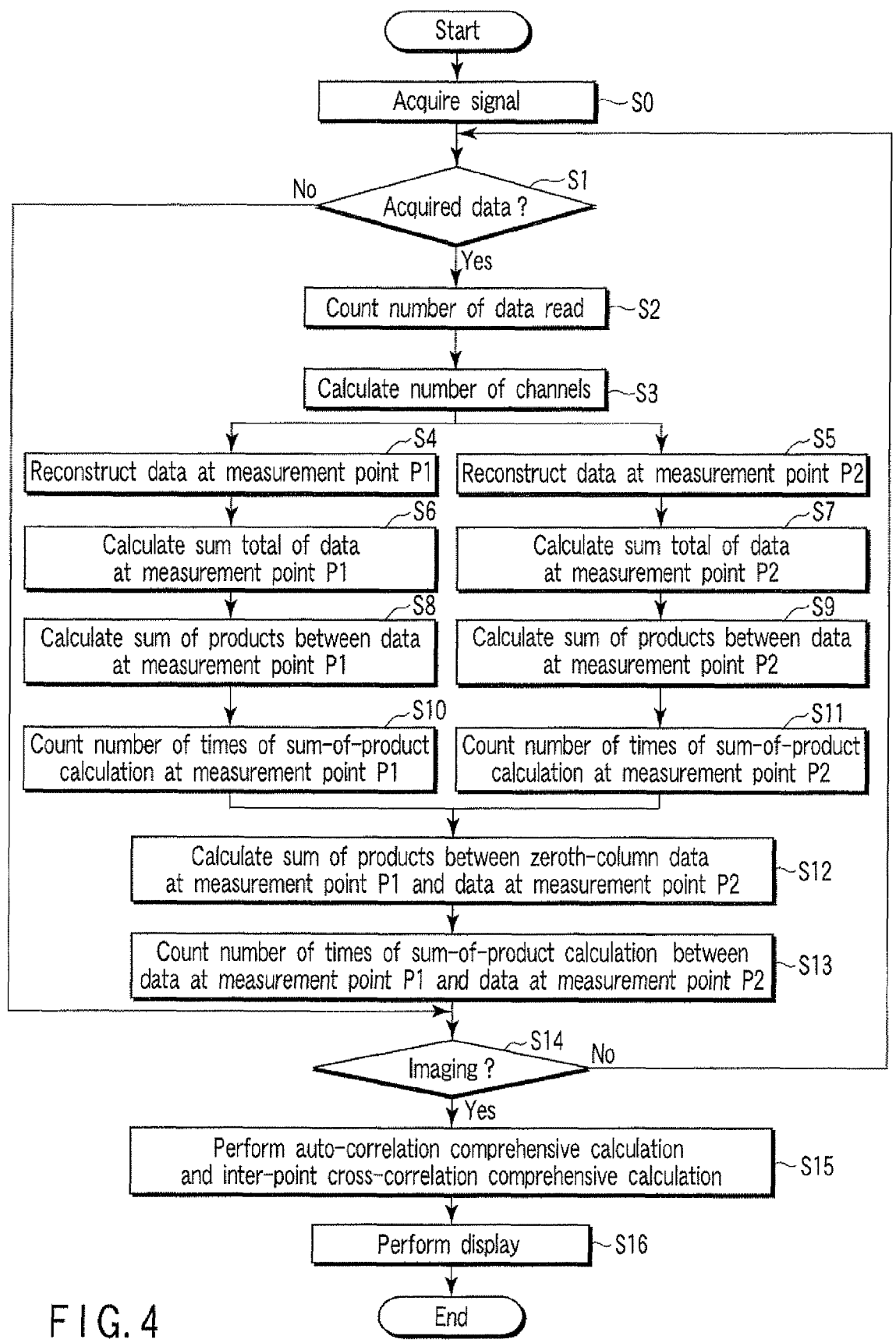
F I G. 4

| Stage 0→t0=τ0 | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| | τ0 | 2τ0 | 3τ0 | 4τ0 | 5τ0 | 6τ0 | 7τ0 | 8τ0 | 9τ0 | 10τ0 | 11τ0 | 12τ0 | 13τ0 | 14τ0 | 15τ0 | 16τ0 |

| Stage 1→t1=2τ0 | 16 | 17 | 18 | 19 | 20 | 21 | 22 | 23 |
|---|---|---|---|---|---|---|---|---|
| | 18τ0 | 20τ0 | 22τ0 | 24τ0 | 26τ0 | 28τ0 | 30τ0 | 32τ0 |

| Stage 2→t2=2τ1 | 24 | 25 | 26 | 27 | 28 | 29 | 30 | 31 |
|---|---|---|---|---|---|---|---|---|
| | 36τ0 | 40τ0 | 44τ0 | 48τ0 | 52τ0 | 56τ0 | 60τ0 | 64τ0 |

| Stage 3→t3=2τ2 | 32 | 33 | 34 | 35 | 36 | 37 | 38 | 39 |
|---|---|---|---|---|---|---|---|---|
| | 72τ0 | 80τ0 | 88τ0 | 96τ0 | 104τ0 | 112τ0 | 120τ0 | 128τ0 |

FIG. 5

Unit : μ

| | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Stage 0→ t0 =2 | 2 | 4 | 6 | 8 | 10 | 12 | 14 | 16 | 18 | 20 | 22 | 24 | 26 | 28 | 30 | 32 |

| | 16 | 17 | 18 | 19 | 20 | 21 | 22 | 23 |
|---|---|---|---|---|---|---|---|---|
| Stage 1→ t1 =2t0 | 36 | 40 | 44 | 48 | 52 | 56 | 60 | 64 |

| | 24 | 25 | 26 | 27 | 28 | 29 | 30 | 31 |
|---|---|---|---|---|---|---|---|---|
| Stage 2→ t2 =2t1 | 72 | 80 | 88 | 96 | 104 | 112 | 120 | 128 |

| | 32 | 33 | 34 | 35 | 36 | 37 | 38 | 39 |
|---|---|---|---|---|---|---|---|---|
| Stage 3→ t3 =2t2 | 144 | 160 | 176 | 192 | 208 | 224 | 240 | 256 |

FIG. 6

Data table for measurement point P2

| 5 | 4 | 6 | 3 | 4 | 4 | 3 | 5 | 3 | 3 | 6 | 4 | 3 | 4 | 5 | 4 |
|---|---|---|---|---|---|---|---|---|---|---|---|---|---|---|---|
| 9 | | 9 | | 8 | | 8 | | 6 | | 10 | | 7 | | 9 | |
| 18 | | | | 16 | | | | 16 | | | | 16 | | | |
| 34 | | | | | | | | 32 | | | | | | | |
| 66 | | | | | | | | | | | | | | | |

Data table for measurement point P1

| 12 | 10 | 10 | 11 | 10 | 11 | 12 | 11 | 10 | 10 | 12 | 11 | 10 | 10 | 12 | 11 |
|---|---|---|---|---|---|---|---|---|---|---|---|---|---|---|---|
| 22 | | 21 | | 21 | | 23 | | 20 | | 23 | | 20 | | 23 | |
| 43 | | | | 44 | | | | 43 | | | | 43 | | | |
| 87 | | | | | | | | 86 | | | | | | | |
| 173 | | | | | | | | | | | | | | | |

FIG. 7

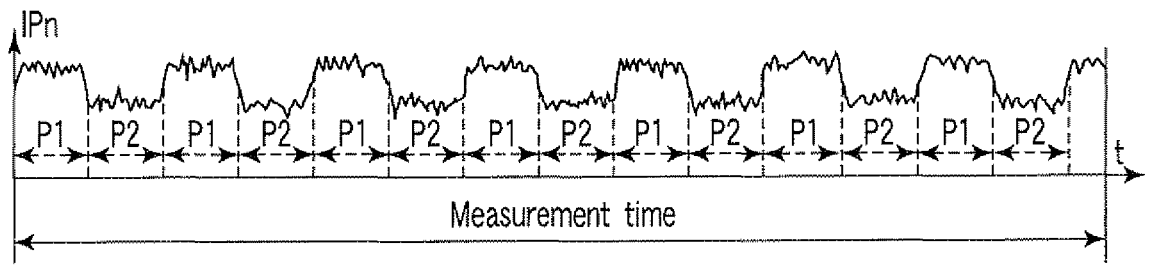
F I G. 11
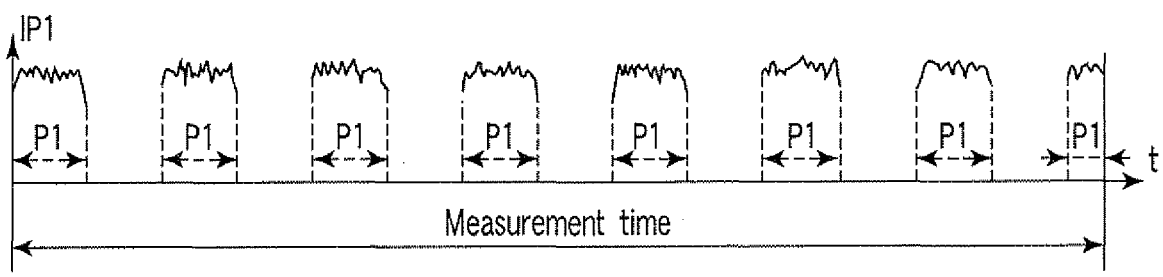
F I G. 12
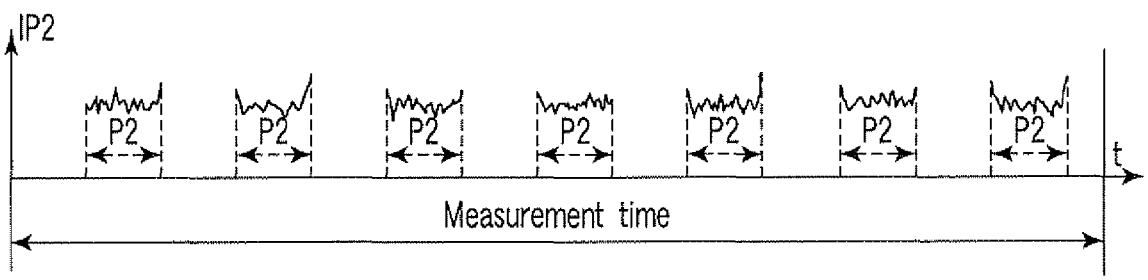
F I G. 13

| Point | 1 | 1 | 1 | 2 | 2 | 2 | 1 | 1 | 1 | 2 | 2 | 2 | 1 | 1 | 1 | 2 | 2 | 2 | ...... |
|---|---|---|---|---|---|---|---|---|---|---|---|---|---|---|---|---|---|---|---|
| Data | 10 | 11 | 10 | 1 | 2 | 1 | 12 | 11 | 10 | 2 | 1 | 2 | 10 | 11 | 10 | 2 | 2 | 1 | ...... |

FIG. 15

| Point | 1 | 1 | 1 | 2 | 2 | 2 | 1 | 1 | 1 | 2 | 2 | 2 | 1 | 1 | 1 | 2 | 2 | 2 | ...... |
|---|---|---|---|---|---|---|---|---|---|---|---|---|---|---|---|---|---|---|---|
| Data | 10 | 11 | 10 | 0 | 0 | 0 | 12 | 11 | 10 | 0 | 0 | 0 | 10 | 11 | 10 | 0 | 0 | 0 | ...... |

FIG. 16

| Point | 1 | 1 | 1 | 2 | 2 | 2 | 1 | 1 | 1 | 2 | 2 | 2 | 1 | 1 | 1 | 2 | 2 | 2 | ...... |
|---|---|---|---|---|---|---|---|---|---|---|---|---|---|---|---|---|---|---|---|
| Data No. | 1 | 1 | 1 | 0 | 0 | 0 | 1 | 1 | 1 | 0 | 0 | 0 | 1 | 1 | 1 | 0 | 0 | 0 | ...... |

FIG. 17

OPTICAL SIGNAL ANALYSIS APPARATUS AND OPTICAL SIGNAL ANALYSIS METHOD

CROSS-REFERENCE TO RELATED APPLICATIONS

This is a Continuation Application of PCT Application No. PCT/JP2006/319133, filed Sep. 27, 2006, which was published under PCT Article 21(2) in Japanese.

This application is based upon and claims the benefit of priority from prior Japanese Patent Application No. 2005-279987, filed Sep. 27, 2005, the entire contents of which are incorporated herein by reference.

BACKGROUND OF THE INVENTION

1. Field of the Invention

The present invention relates to an optical signal analysis apparatus and an optical signal analysis method.

2. Description of the Related Art

Optical signal analysis methods are disclosed in, for example, Klaus Sch-tzel, "New Concept in Correlator Design", Inst. Phys. Conf. Ser. No. 77, P175, 1985, Klaus Sch-tzel, "Noise on Multiple-Tau Photon Correlation Data", SPIE Vol. 1430, P109, Photon Correlation Spectroscopy Multicomponent Systems, 1991, and Klaus Sch-tzel et al., "Photon Correlation Measurements at Large Lag Times", Journal of Modern Optics, Vol. 35, No. 4, P711, 1988. In these optical signal analysis methods, an auto-correlation function or a cross-correlation function is estimated by using either the continuous measurement data (continuous measurement signal) of the intensity of fluorescence obtained from only one measurement point in one measurement or the plural-point time-series mixed data (multiple-point time-series mixed signal) measured while measurement points are repeatedly switched with time. As an analysis algorithm, a calculation technique based on a multiple τ scheme or a table retrieval scheme is available. When there is only one measurement point, an algorithm called a general scheme or a single measurement point multiple τ scheme is used. That is, the calculation technique based on the single measurement point multiple τ scheme estimates an auto-correlation function or a cross-correlation function at a measurement point through data processing such as channel calculation or data reconstruction. When measurement points are to be measured in one measurement, an algorithm called a general scheme or a table retrieval scheme is used. That is, the table retrieval scheme simultaneously estimates auto-correlation functions or cross-correlation functions for measurement points through high-speed data processing based on the time division of data at the respective measurement points and pieces of position information at the measurement points that are formed into a table.

Yoshiaki Horikawa, "For Single Molecular Fluorescence Analysis/Analysis on Single Biomolecular Interaction Using Statistical Analysis", Bunko Kenkyu, Vol. 53, No. 3, 158-164, 2004 discloses a photo counting histogram method.

Kazuhiko Mase, Mitsuru Nagasono, Shinichiro Tanaka, and Shinichi Nagaoka, "Study of ion desorption induced by core-electron excitations of molecules on surface by using electron-ion coincidence spectroscopy", Hoshasen, 10, 375-391, 1997 discloses a coincidence analysis method.

However, the purpose of estimating an auto-correlation function and a cross-correlation function at one measurement point is to observe molecular diffusion with a relatively low diffusion rate in a microscopic area. In actual application, when, for example, a molecule passes through the nuclear membrane of a cell, the molecular diffusion rate is low, and the diffusion time is long. It is impossible to observe the transmission of a signal, the influence of molecular movement in a given direction, and the like by auto-correlation and cross-correlation based on observation at only one point.

That is, according to the prior art, an observation area is limited to one measurement point (confocal volume). In addition, the movement of a molecule between two or more points cannot be observed. Furthermore, slow molecular diffusion cannot be observed.

BRIEF SUMMARY OF THE INVENTION

An optical signal analysis apparatus according to the present invention includes a photodetector to detect light emitted from measurement points in a sample, and analyzer to analyze a molecular interaction between two of the measurement points by using fluctuation signals corresponding to fluctuations of light from the measurement points that are detected by the photodetector.

An optical signal analysis method according to the present invention includes a photodetection step of detecting light emitted from measurement points in a sample, and an analysis step of analyzing a molecular interaction between two of the measurement points by using fluctuation signals corresponding to fluctuations of light from the measurement points.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is a flowchart showing analysis processing by a data analysis unit in FIG. 1;

FIG. 5 is a view showing the structure and values of channels;

FIG. 6 is a view showing the structure and values of channels with a bin time of 2 µs;

FIG. 7 is a view showing data reconstruction at the measurement point P1 and the measurement point P2 in the continuous signals in FIGS. 2 and 3;

FIG. 11 is a view showing a time-series mixed signal containing fluctuation signals corresponding to the fluctuations of light from the measurement point P1 and the measurement point P2 obtained in the apparatus in FIG. 10;

FIG. 12 is a view showing a time-division signal at the measurement point P1 that is extracted from the time-series mixed signal in FIG. 11;

FIG. 13 is a view showing a time-division signal at the measurement point P2 that is extracted from the time-series mixed signal in FIG. 11;

FIG. 15 is a view showing mixed data at the measurement point P1 and the measurement point P2 that corresponds to the time-series mixed signal in FIG. 11;

FIG. 16 is a view showing division data at the measurement point P1 that corresponds to the time-division signal in FIG. 12;

FIG. 17 is a view showing division weighting coefficients at the measurement point P1 that correspond to the division data in FIG. 16;

DETAILED DESCRIPTION OF THE INVENTION

The embodiments of the present invention will be described below with reference to the views of the accompanying drawing.

First Embodiment

Figure 1:
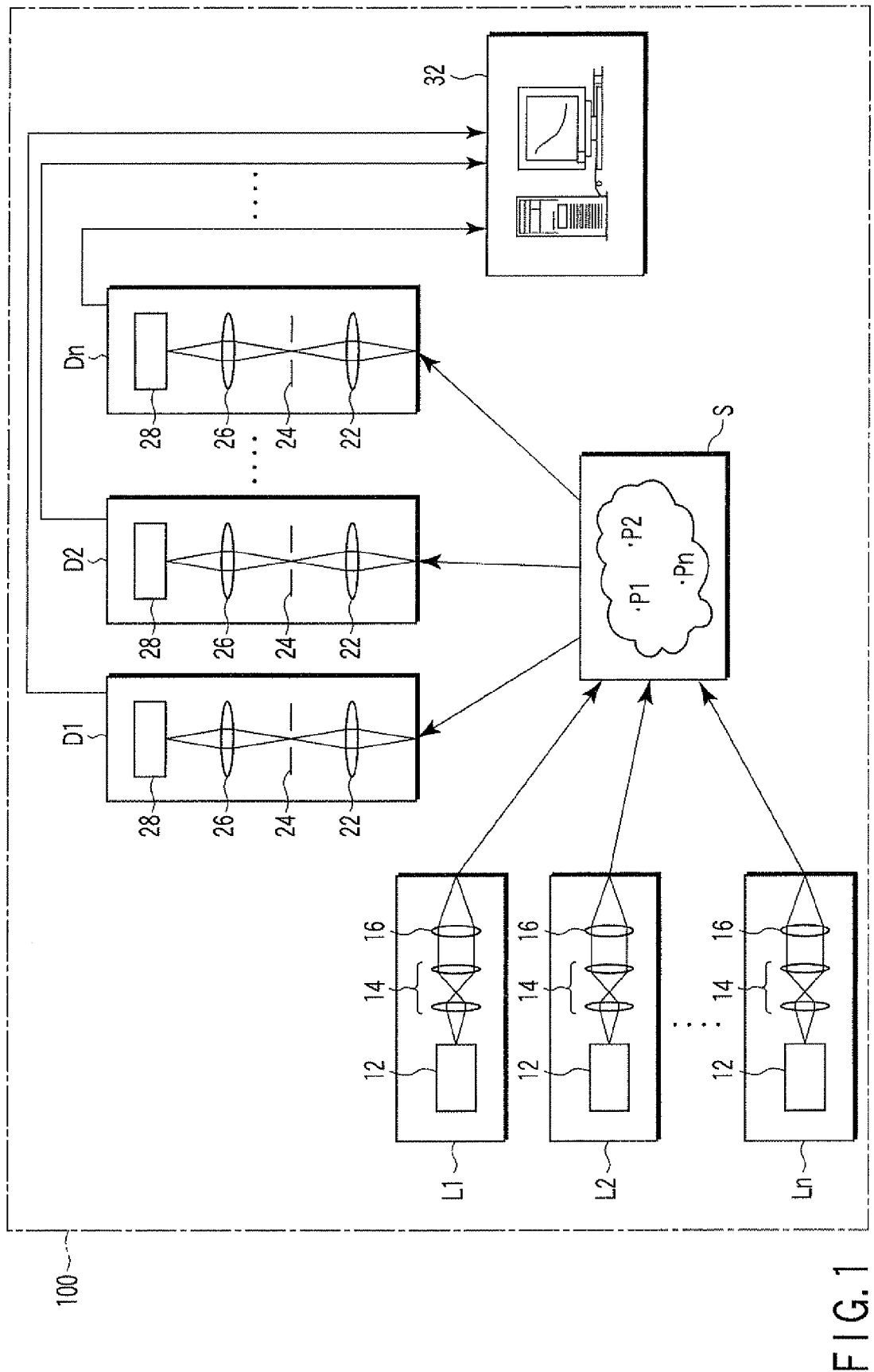
FIG. 1 is a view schematically showing an optical signal analysis apparatus according to the first embodiment of the present invention.

FIG. 1 schematically shows an optical signal analysis apparatus according to the first embodiment of the present invention. An optical signal analysis apparatus 100 includes light applying units L1, L2, ..., Ln, photodetection units D1, D2, ..., Dn, and a data analysis unit 32.

Each of the light applying units L1, L2, ..., Ln includes a light source 12, a collimating lens 14, a condenser lens 16, and the like. The light applying units L1, L2, ..., Ln continuously apply excitation light to different measurement points P1, P2, ..., Pn in a sample S.

Each of the photodetection units D1, D2, ..., Dn includes a condenser lens 22, a pinhole 24, an imaging lens 26, a photodetector 28, and the like. The photodetection units D1, D2, ..., Dn respectively receive light emitted from the measurement points P1, P2, ..., Pn. More specifically, the pinholes 24 are placed at positions conjugate to the measurement points P1, P2, ..., Pn. The imaging lenses 26 respectively project the images of the pinholes 24 onto the photodetectors 28. Thus, only the light emitted from the measurement points P1, P2, ..., Pn selectively strike the photodetectors 28. The photodetectors 28 respectively output continuous measurement data reflecting the intensities of incident light, i.e., fluctuation signals corresponding to the fluctuations of the light from the measurement points P1, P2, ..., Pn.

As is obvious from the above description, the photodetection units D1, D2, ..., Dn constitute a photodetector to detect light emitted from the measurement points P1, P2, ..., Pn. The light applying units L1, L2, ..., Ln constitute an excitation light applier to continuously apply excitation light to the measurement points P1, P2, ..., Pn, respectively.

The data analysis unit 32, which is constituted by, for example, a personal computer, estimates auto-correlation functions and cross-correlation functions for fluctuation signals output from the photodetectors 28. That is, the data analysis unit 32 estimates an auto-correlation function at each of the measurement points P1, P2, ..., Pn, and also estimates a cross-correlation function between two of the measurement points P1, P2, ..., Pn. That is, the data analysis unit 32 constitutes an analyzer to analyze a molecular interaction such as the movement vector of a molecule between two of the measurement points P1, P2, ..., Pn by using fluctuation signals corresponding to the fluctuations of light from the measurement points P1, P2, ..., Pn that are detected by the photodetection units D1, D2, ..., Dn. The data analysis unit 32 also displays and stores the analysis results. Among the continuous data (continuous signals) at the measurement points P1, P2, ..., Pn, continuous data (continuous signals) at two independent measurement points are used for inter-point correlation computation. At different measurement points, continuous data (signals) are measured, and a correlation relationship in the vector direction between the two points is directly observed from changes in molecular movement.

Figure 2:
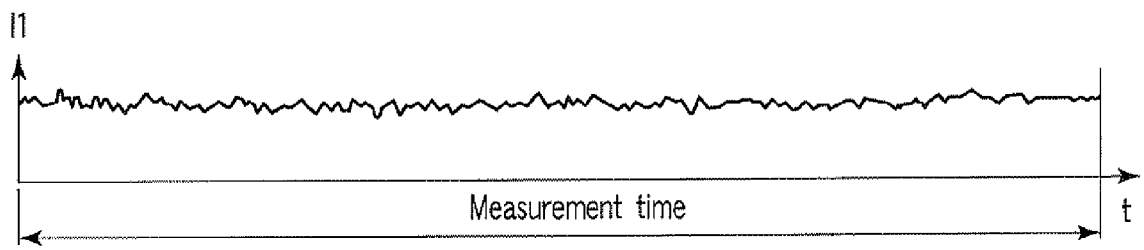
FIG. 2 is a view showing a fluctuation signal corresponding to the fluctuations of light from a measurement point P1 that is obtained in the apparatus in FIG. 1.
Figure 3:
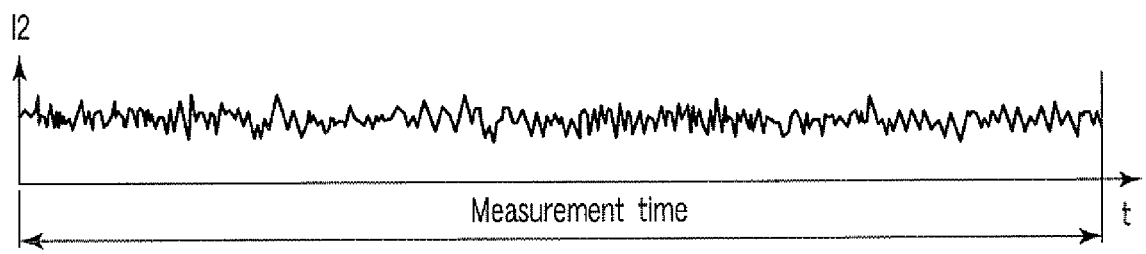
FIG. 3 is a view showing a fluctuation signal corresponding to the fluctuations of light from a measurement point P2 that is obtained in the apparatus in FIG. 1.
Figure 8:
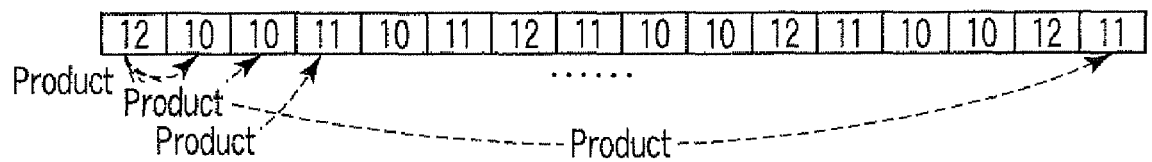
FIG. 8 is a view showing sum-of-product calculation between data at the measurement point P1 in the continuous signals in FIGS. 2 and 3.

Analysis at the two measurement points P1 and P2 will be exemplified below. FIG. 2 shows a fluctuation signal corresponding to the fluctuations of light from a measurement point. FIG. 3 shows a fluctuation signal corresponding to the fluctuations of light from a measurement point.

Analysis processing by the data analysis unit 32 will be described below with reference to the flowchart of FIG. 4.

[Step S0]

As measurement data about a sample, digital data at the two measurement points P1 and P2, i.e., fluctuation signals of light at the two measurement points P1 and P2, are acquired. Although the acquired digital data at the two measurement points P1 and P2 are directly used for calculation, the data can be displayed as the continuous signals shown in FIGS. 2 and 3 by an interpolation method.

[Step S1]

Whether there is any acquired data is determined. If YES, the process advances to step S2. If NO, the process enters the imaging determination in step S14.

[Step S2]

The number of data read is counted. The total number of data counted is used for channel calculation, comprehensive calculation, and the like.

[Step S3]

For example, plotted τ values (channel values) and the number of channels in the multiple τ scheme are calculated. The multiple τ scheme determines the number of channels from the total number of data read. FIG. 5 shows a specific calculation method. The first 16 channel values are based on a bin time $\tau_0$ as a reference value, and every subsequent eighth channel value is based on the value obtained by doubling the bin time $\tau_0$ as a reference value. FIG. 5 shows general channel values based on the bin time $\tau_0$ as a reference value. FIG. 6 shows channel values when the bin time $\tau_0$ is 2 μs.

In other words, the first 16 channels are set in the zeroth stage, and subsequent sets of eight channels each are set in the first stage, second stage, .... An increment (reference value) in channel value in each stage is represented by $2^n\tau_0$ where n is the number of stages. For example, an increment in channel value in the zeroth stage is $\tau_0$, and an increment in channel value in the second stage is $4\tau_0$.

As is obvious from the above description, the number of channels for correlation value calculation is calculated on the basis of bin times and the total number of data read. For example, when data is measured for 32 sec with a bin time of 2 µs, the total number of channels for calculation is approximately 176.

[Steps S4 and S5]

In step S4, data reconstruction at the measurement point P1 is performed. In step S5, data reconstruction at the measurement point P2 is performed. That is, the first channel data of the respective channels with different reference values (increments) is calculated. Summation processing for measurement data $I_{P1}$ and $I_{P2}$ at the measurement point P1 and the measurement point P2 is performed. With regard to a delay time τ after channel 16, since the reference (increment) is doubled for every eighth channel (see step S3), the data of each channel comprises the sum of two data before the reference value (increment) is doubled. Changes in data in detail are shown in FIG. 7. Performing summation processing at each of the two measurement points P1 and P2 will sequentially generate channel data having new reference values (increments) from acquired data, thereby generating a new data form. In actual data reconstruction processing, the data of a channel other than the first channel is formed by moving the data of the first channel.

In other words, the array of all the read data is set as the data array of the zeroth row, and the array of the sums of pairs of adjacent data is set as the data array of the first row. Subsequently, the same operation is repeated to generate the data arrays of the second row, third row, .... This operation is repeated until data arrays equal in number to channel stages are obtained. In each data table obtained in this manner, the data of each row correspond to the channels in a corresponding stage. For example, the second-row zeroth-column data corresponds to the second-stage zeroth-column channel.

[Steps S6 and S7]

The sum total of data is calculated. That is, the sum totals of data with variables at the respective channel value positions in the multiple τ scheme is calculated with respect to the measurement data $I_{P1}$ and $I_{P2}$ at the measurement point P1 and the measurement point P2.

[Steps S8 and S9]

Sum-of-product calculation between data at the same measurement point is performed. That is, for the measurement data $I_{P1}$ and $I_{P2}$ at the measurement point P1 and the measurement point P2, in the case of the measurement point P1, data at channel positions with the same reference value (increment) is multiplied by the zeroth-column data, and the sum of the products is calculated. In other words, in the data array at the measurement point P1 that corresponds to the channels of each stage shown in FIG. 5, the sum of the products between the first data and the respective remaining data is obtained. Similar calculation processing is performed for the measurement point P2.

[Steps S10 and S11]

The number of times of data sum-of-product calculation at the same measurement point is counted. That is, count of the number of times of data sum-of-product calculation is performed at the same time as calculation in steps S8 and S9.

[Step S12]

Figure 9:
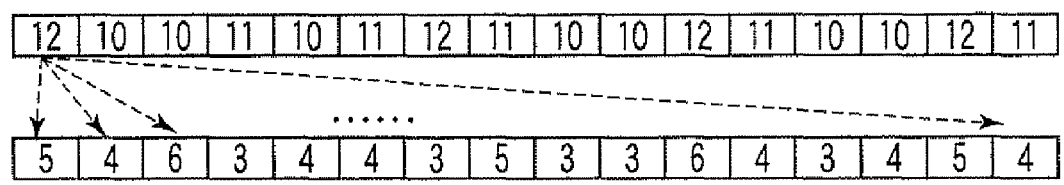
FIG. 9 is a view showing sum-of-product calculation between data at the measurement point P1 and the measurement point P2 in the continuous signals in FIGS. 2 and 3.

Sum-of-product calculation of data between different measurement points is performed. That is, sum-of-product calculation between the zeroth-column data at the measurement point P1 and the data at the measurement point P2 is performed. As shown in FIG. 9, the data at channel positions with the same reference value (increment) as that at the measurement point P2 is multiplied by the zeroth-column data at the measurement point P1, and the sum of products is calculated. In other words, for the data array at the measurement point P1 and the data array at the measurement point P2 that correspond to the channels of the respective stages, the sum of the products between the first data of the data array at the measurement point P1 and the respective data of the data array at the measurement point P2 is obtained.

[Step S13]

The number of times of data sum-of-product calculation between different measurement points is counted. That is, count of the number of times of data sum-of-product calculation is performed at the same time as calculation in step S12.

[Step S14]

Termination of the computation and imaging are determined. If YES, the process enters comprehensive correlation calculation in step S15. If NO, the process returns to the data acquisition determination in step S1.

[Step S15]

If the data read is complete (YES in step S14), auto-correlation functions for each of the two measurement points P1 and P2 and an inter-point cross-correlation function between the two measurement points P1 and P2 are estimated on the basis of the above respective calculation results. That is, correlation functions are estimated by using different analytical expressions for the respective correlation directions of P1→P2, P1→P1, and P2→P2.

For example, the formula (S8*S10)/(S60*S6) is used for P1→P1, the formula (S9*S11)/(S60*S7) is used for P2→P2, and the formula (S12*S13)/(S60*S6) is used for P1→P2. Here, S60 and S70 represent data sum totals at channel positions with the respective reference values (increments).

These analytical expressions can be expressed by $$C(\tau) = \frac{mlF_{P1}R_{P1}\mathrm{Sum}(\tau_\nu) * mlN_{P1P1}\mathrm{Sum}(\tau_\nu)}{mlF_{P1}0\mathrm{Sum}(\tau_\nu) * mlF_{P1}\mathrm{Sum}(\tau_\nu)} \quad (1)$$

$$C(\tau) = \frac{mlF_{P2}R_{P2}\mathrm{Sum}(\tau_\nu) * mlN_{P2P2}\mathrm{Sum}(\tau_\nu)}{mlF_{P2}0\mathrm{Sum}(\tau_\nu) * mlF_{P2}\mathrm{Sum}(\tau_\nu)} \quad (2)$$

$$C(\tau) = \frac{mlF_{P1}R_{P2}\mathrm{Sum}(\tau_\nu) * mlN_{P1P2}\mathrm{Sum}(\tau_\nu)}{mlF_{P1}0\mathrm{Sum}(\tau_\nu) * mlF_{P2}\mathrm{Sum}(\tau_\nu)} \quad (3)$$

In equations (1) to (3), $mlF_P0\mathrm{Sum}(\tau_\nu)$ represents the sum total of zeroth-column data of the respective stages, $mlF_P\mathrm{Sum}(\tau_\nu)$ represents the sum total of channel data in each multiple τ scheme, $mlF_PR_P\mathrm{Sum}(\tau_\nu)$ represents sum-of-product calculation between zeroth-column data and the respective channel data, and $mlN_{PP}\mathrm{Sum}(\tau_\nu)$ represents the total number of times of sum-of-product calculation. Here the subscript P is P1 or P2, and corresponds to calculation target data, i.e., data at the measurement point P1 or data at the measurement point P2.

[Step S16]

Processing such as displaying an inter-point cross-correlation function in the form of a curve is performed on the basis of each final calculation result.

As is obvious from the above description, the photometric analysis apparatus of this embodiment estimates cross-correlation functions for the two different measurement points P1 and P2. If the correlation of the analysis result on P1→P2 is high, it can be estimated that the probability of movement of the same molecule from the measurement point P1 to the measurement point P2 is high. In contrast, if the correlation is low, it can be estimated that the probability of passage of a molecule through the measurement point P2 after passage through the measurement point P1 is low, and the probability of movement of the molecule in another direction is high. That is, the photometric analysis apparatus of the embodiment allows observation of the movement of a molecule between the two measurement points P1 and P2. In addition, by examining the correlativity between sets of two measurement points, molecular movement vectors are estimated.

Second Embodiment

Figure 10:
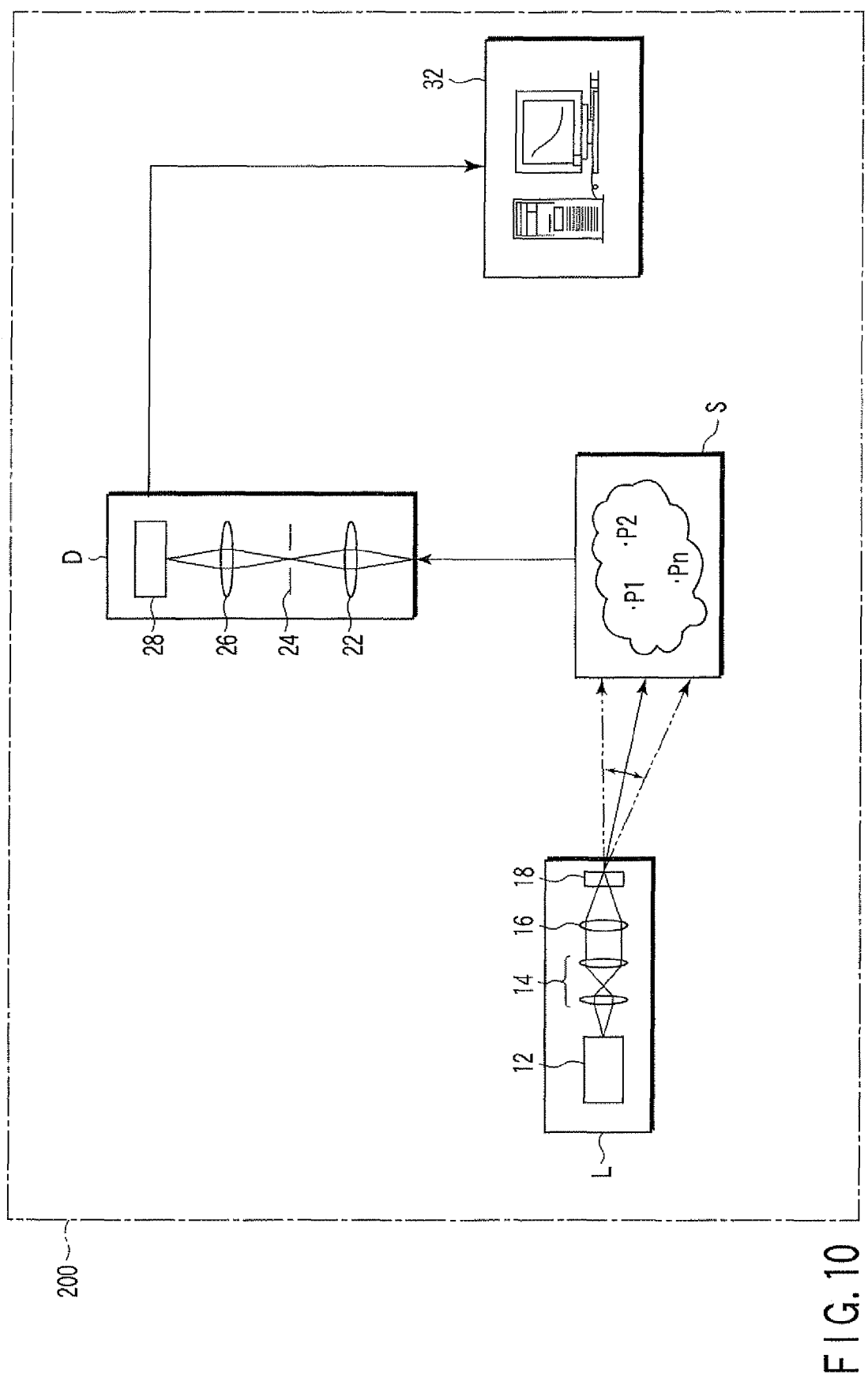
FIG. 10 is a view schematically showing an optical signal analysis apparatus according to the second embodiment of the present invention.

FIG. 10 schematically shows an optical signal analysis apparatus according to the second embodiment of the present invention. An optical signal analysis apparatus 200 includes a single light applying unit L, a single photodetection unit D, and a data analysis unit 32.

The light applying unit L includes a light source 12, a collimating lens 14, a condenser lens 16, a scanner 18, and the like. The light applying unit L, which is an excitation light applier to time-divisionally apply excitation light to measurement points P1, P2, . . . , Pn, intermittently scans a light beam by the scanner 18, and applies excitation light to the different measurement points P1, P2, . . . , Pn in a sample S.

The photodetection unit D includes a condenser lens 22, a pinhole 24, an imaging lens 26, a photodetector 28, and the like. The photodetection unit D, which is a a photodetector to time-divisionally detect light emitted from the measurement points P1, P2, . . . , Pn in the sample, time-serially receives light emitted from the measurement points P1, P2, . . . , Pn. The arrangement of the photodetection unit D is the same as that of one of the photodetection units D1, D2, . . . , Dn in the first embodiment.

The data analysis unit 32 comprises, for example, a personal computer. The data analysis unit 32 estimates an autocorrelation function at each of the measurement points P1, P2, . . . , Pn and a cross-correlation function between two of the measurement points P1, P2, . . . , Pn on the basis of the fluctuation signals output from the photodetector 28. That is, the data analysis unit 32 constitutes an analyzer to analyze a molecular interaction such as the movement vector of a molecule between two of the measurement points P1, P2, . . . , Pn by using fluctuation signals corresponding to the fluctuations of light from the measurement points P1, P2, . . . , Pn that are time-divisionally detected by the photodetection unit D.

The following exemplifies analysis at the two measurement points P1 and P2. The light applying unit L alternately applies excitation light to the two measurement points P1 and P2 at short time intervals. As shown in FIG. 11, thus, data from the photodetection unit D becomes time-series mixed data in which data at the two measurement points P1 and P2 are alternately mixed. Reference symbols P1 and P2 in FIG. 11 respectively denote data measurement ranges for the measurement points P1 and P2. That is, this data alternately contains the data at the measurement point P1 and the measurement point P2, and can be divided by time. Although the time-series mixed data actually includes measurement ranges in switching periods between the measurement points P1 and P2 in addition to the data measurement ranges for the measurement points P1 and P2, FIG. 11 does not illustrate them.

This time-series mixed data is sent to the data analysis unit 32 to be divided into data at each measurement point and processed. That is, the data analysis unit 32 extracts the time-division data at the measurement point P1 shown in FIG. 12 and the time-division data at the measurement point P2 shown in FIG. 13 from the time-series mixed data shown in FIG. 11. Consider the time-division data at the measurement point P1. The data at the measurement point P1 are obtained by extracting only fluorescence intensity in each period during which the scanner 18 stops an excitation light beam at the measurement point P1, and data in other periods are set as 0. Likewise, with regard to the signal at the measurement point P2, the data at the measurement point P2 are obtained by extracting only fluorescence intensity in each period during which the scanner 18 stops an excitation light beam at the measurement point P2, and data in other periods are set as 0. In this manner, the data analysis unit 32 generates two pseudo signals or pseudo data corresponding to light from the measurement point P1 and the measurement point P2 on the basis of the fluctuation signals output from the photodetector 28. In this pseudo signal or pseudo data, each signal omission period that occurs due to time-divisional detection is interpolated by a signal with a predetermined value.

That is, data at two different measurement points are extracted from time-series mixed data at the two measurement points. The data analysis unit 32 performs inter-point correlation computation for the extracted data at the two different measurement points by using the conventional general-purpose scheme, the information table scheme, or the multiple τ scheme.

In this embodiment, when performing data analysis on inter-point cross-correlation functions in the multiple τ scheme using weighting coefficients, the data analysis unit repeatedly performs measurement at two measurement points. The data analysis unit extracts only data and weighting coefficients corresponding to each measurement point by time-serially dividing the measurement data obtained by measurement into a data table and a weighting coefficient table at each measurement point, thereby calculating an autocorrelation function. The data analysis unit calculates autocorrelation functions and inter-point cross-correlation functions by using the extracted data at the respective measurement points, the data at the two measurement points in the weighting coefficients, and the weighting coefficients. Based on the calculation result, an operator simultaneously observes not only cell reactions at two points but also a cell interaction between different regions (two points).

When correlation function computation is performed, octave channels are used as channels for the calculation of data and weighting coefficients, and the calculation of data and weighting coefficients is limited to the result obtained by a small finite number of channels, thereby implementing the plotting of calculation results at equal intervals. In addition, the data analysis unit calculates the average of data and the average of weighting coefficients that correspond to different delay times in different τ areas in advance. Assume that in each process using the extracted data and weighting coefficients at measurement points, one data or weighting coefficient is set as a minimum calculation unit.

Figure 14A:
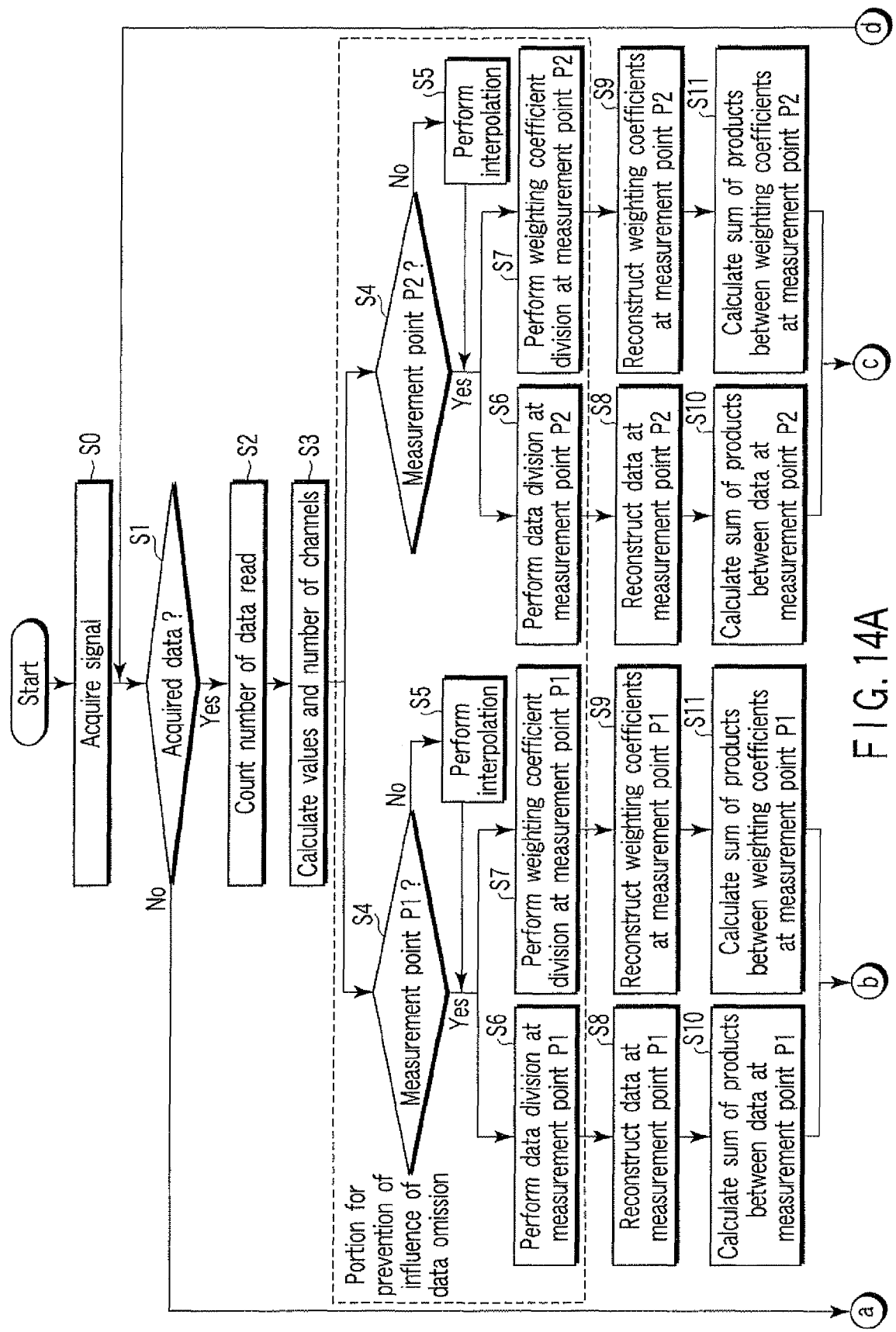
FIG. 14A is a view showing part of a flowchart for analysis processing by the data analysis unit in FIG. 10.
Figure 14B:
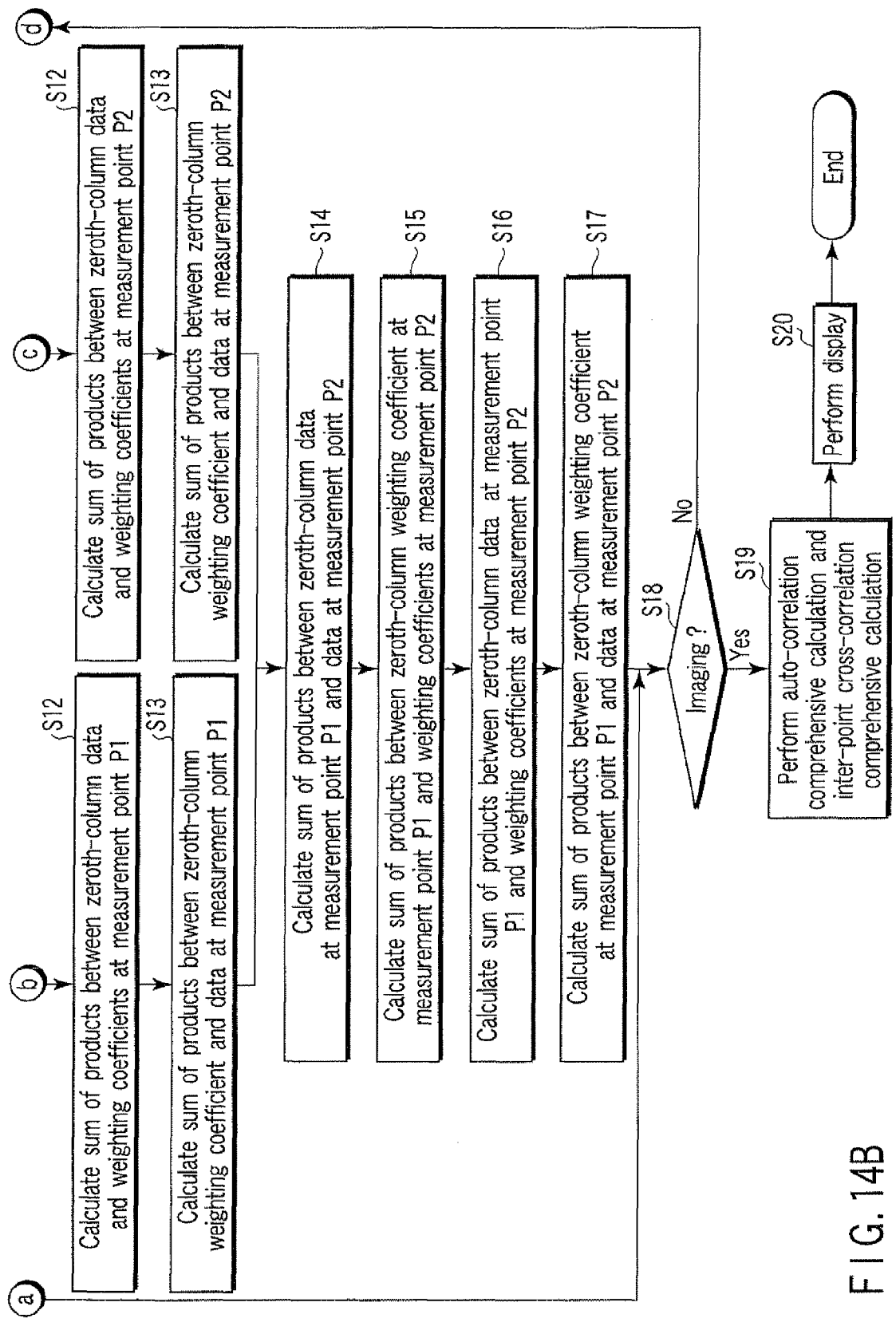
FIG. 14B is a view showing part of the flowchart for analysis processing by the data analysis unit in FIG. 10.

The multiple τ scheme will be described in detail below with reference to the flowcharts of FIGS. 14A and 14B.

[Step S0]

As measurement data about a sample, the time-series measurement data at the two measurement points P1 and P2 are acquired. A continuous signal obtained by an interpolation method for the acquired time-series mixed data is shown FIG. 11.

[Step S1]

Whether there is any acquired data is determined. IF YES, the process advances to step S2. If NO, the process enters the imaging determination in step S18.

[Step S2]

The number of data read is counted. The total number of data counted is used for channel calculation, comprehensive calculation, and the like.

[Step S3]

For example, plotted $\tau$ values (channel values) and the number of channels in the multiple $\tau$ scheme are calculated. The multiple $\tau$ scheme determines the number of channels from the total number of data read. According to a specific calculation method, as shown in FIG. 5 in the first embodiment, the first 16 channel values are based on a bin time $\tau_0$ as a reference value, and every subsequent eighth channel value is based on the value obtained by doubling the bin time $\tau_0$ as a reference value.

In other words, the first 16 channels are set in the zeroth stage, and subsequent sets of eight channels each are set in the first stage, second stage, . . . . An increment (reference value) in channel value in each stage is represented by $2^n\tau_0$ where n is the number of stages. For example, an increment in channel value in the zeroth stage is $\tau_0$, and an increment in channel value in the second stage is $4\tau_0$.

As is obvious from the above description, the number of channels for calculation is determined by bin time values and the total number of data read.

[Steps S4 and S5]

Measurement points are identified. That is, the number of measurement points at which measurement has been simultaneously performed and the corresponding measurement point numbers are determined. If it is determined in step S4 that the measurement point is the measurement point P1, the input data is processed as the effective data at the measurement point P1 in step S6 and the subsequent steps, and data at the measurement point P2 is processed as zero in step S5. If it is determined in step S4 that the measurement point is the measurement point P2, the input data is processed as the effective data at the measurement point P2 in step S6 and the subsequent steps, and data at the measurement point P1 is processed as zero in step S5. If the measurement point is neither the measurement point P1 nor the measurement point P2, the data at the measurement point P1 is interpolated as zero in step S5 as in the above case.

[Step S6]

Data extraction is performed. That is, the data analysis unit divides data at each measurement point. When measurement is performed at measurement points while the measurement points are time-serially switched, time-series mixed data in which data at the measurement points are mixed is obtained. Here, the time-series mixed data is divided into data at each measurement point. If, for example, data measurement is performed at the measurement points P1 and P2 in the order of P1→P2→P1 as in the case shown in FIG. 11, two measurement data at the measurement points P1 and P2 are time-serially arrayed in the measured data. This data is expressed by a specific data table like that shown in FIG. 15, and a data division method for each measurement point will be described. First of all, at the measurement point P1, only the data at the measurement point P1 is extracted from the mixed data. Data 0 is then embedded at a position corresponding to the other measurement point (the measurement point P2). As a result, the division data table for the measurement point P1 shown in FIG. 16 is generated. Likewise, the data analysis unit generates a different data table for the measurement point P2. That is, two pseudo data corresponding to the respective light are generated from the two measurement points P1 and P2 on the basis of the fluctuation signals output from the photodetector 28. In this pseudo data, each signal omission period that occurs due to time-divisional detection is interpolated by data with a predetermined value. As a result, two division data tables are generated at the two measurement points P1 and P2.

[Step S7]

In order to prevent the influence of each signal or data omission period that occurs due to time-divisional detection, different weights are assigned between each period during which a signal or data is omitted and each of other periods. A weighting coefficient table for this purpose is generated. That is, weighting coefficient division is performed for each measurement point. When measurement is performed at measurement points while the measurement points are time-serially switched, the measurement data contains information representing the size of data and information representing the measurement point position of data. Such information is also divided at each measurement point. The multiple $\tau$ scheme based on measurement at plural measurement points uses such information as weighting coefficients for calculation. When data measurement is performed at the two measurement points P1 and P2, the resultant data is represented by one data (weighting coefficient=1). First of all, only weighting coefficients corresponding to the measurement point P1 are extracted as in the case of data signal division. A weighting coefficient of 0 is embedded at each position corresponding to the other measurement point. As a consequence, the division weighting coefficient table for the measurement point P1 shown in FIG. 17 is generated. Likewise, a different division weighting coefficient table for the measurement point P2 is generated. That is, two division weighting coefficient tables at the two measurement points P1 and P2 are generated.

[Step S8]

Figure 18:
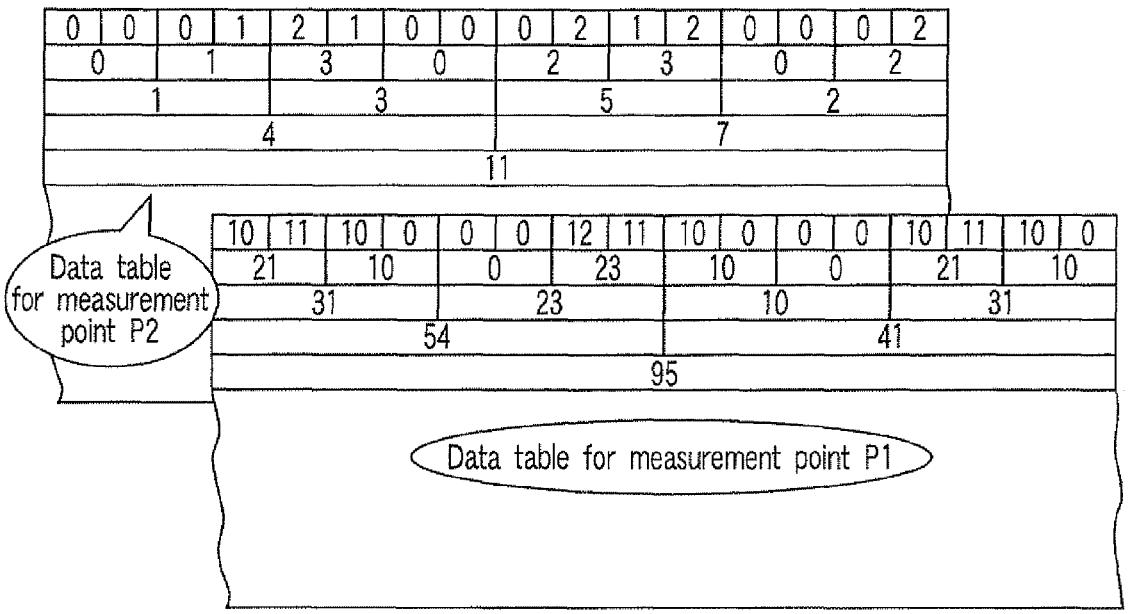
FIG. 18 is a view showing data tables obtained by reconstructing division data at the measurement point P1 and the measurement point P2.

Data reconstruction is performed. That is, the first channel data of the respective channels with different reference values (increments) is calculated. Summation processing at each measurement point is performed by using the data tables for the measurement point P1 and the measurement point P2. With regard to a delay time $\tau$ after channel 16, since the reference (increment) is doubled for every eighth channel (see steps S4 and S5 in the first embodiment), the data of each channel comprises the sum of two data before the reference value (increment) is doubled. Changes in data in detail are shown in FIG. 18. Performing summation processing at the two measurement points P1 and P2 will sequentially generate channel data having new reference values (increments) from data division tables, thereby generating a new data form.

In other words, the array of all the read data is set as the data array of zeroth row, and the array of the sums of pairs of adjacent data is set as the data array of the first row. Subsequently, the same operation is repeated to generate the data arrays of the second row, third row, . . . . This operation is repeated until data arrays equal in number to channel stages are obtained. In each data table obtained in this manner, the data of each row correspond to the channels in a corresponding stage. For example, the second-row zeroth-column data corresponds to the second-stage zeroth-column channel.

[Step S9]

Figure 19:
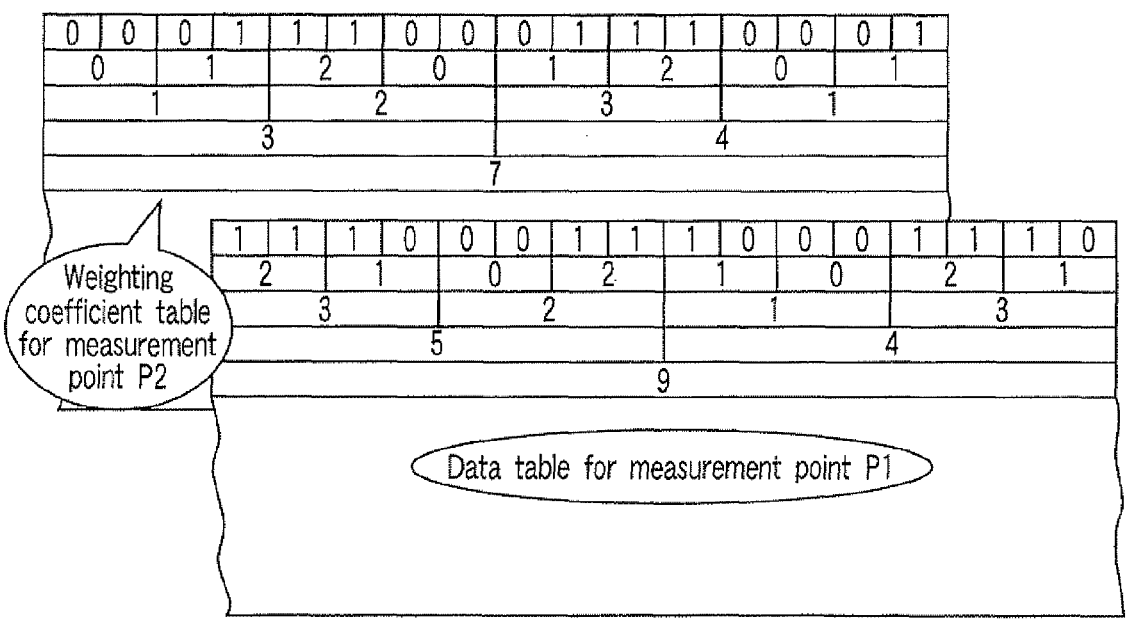
FIG. 19 is a view showing weighting coefficient tables obtained by reconstructing division weighting coefficients at the measurement point P1 and the measurement point P2.

Weighting coefficient reconstruction is performed. That is, the first channel weighting coefficients of respective channels with different reference values (increments) is calculated. Summation processing is performed for each measurement point by using the division weighting coefficient tables for the measurement point P1 and the measurement point P2. The weighting coefficient tables change in the same manner as in step S8. That is, in the process of summation processing, weighting coefficients for channels with new reference values (increments) are sequentially formed (FIG. 19), thereby generating a new weighting coefficient form.

In other words, the array of all weighting coefficients is set as the weighting coefficient array of the zeroth row, and the array of the sums of pairs of adjacent weighting coefficients is set as the weighting coefficient array of the first row. Subsequently, this operation is repeated to generate the weighting coefficient arrays of the second row, third row, . . . . This operation is repeated until weighting coefficient arrays equal in number to channel stages are obtained. In each weighting coefficient table obtained in this manner, the weighting coefficients of each row correspond to the channels in a corresponding stage.

[Step S10]

Figure 20:
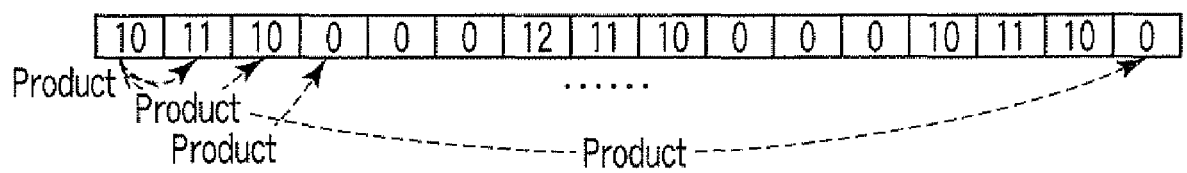
FIG. 20 is a view showing sum-of-product calculation between data at the measurement point P1.

Sum-of-product calculation between data is performed for extracted data $I_{P1}$ at the measurement point P1. That is, as shown in FIG. 20, data at channel positions of the measurement point P1 at which the same reference value (increment) is set is multiplied by the zeroth-column data, and the sum of the products is calculated. In other words, in the data array at the measurement point P1 that corresponds to the channels of each stage, the sum of the products between the first data and the respective remaining data is obtained. Sum-of-product calculation between data is then performed for extracted data $I_{P2}$ at the measurement point P2. That is, the same processing is performed at the measurement point P2, so that data at channel positions of the measurement point P2 at which the same reference value (increment) is set is multiplied by the zeroth-column data, and the sum of the products is calculated. In other words, in the data array at the measurement point P2 that corresponds to the channels of each stage, the sum of the products between the first data and the respective remaining data is obtained.

[Step S11]

Sum-of-product calculation between weighting coefficients is performed for extracted weighting coefficients $W_{P1}$ at the measurement point P1. That is, weighting coefficients at channel positions of the measurement point P1 at which the same reference value (increment) is set are multiplied by the zeroth-column weighting coefficient, and the sum of the products is calculated. In other words, in the weighting coefficient array at the measurement point P1 that corresponds to the channels of each stage, the sum of the products between the first weighting coefficient and the respective remaining weighting coefficients is obtained. Sum-of-product calculation between weighting coefficients is then performed for extracted weighting coefficients $W_{P2}$ at the measurement point P2. That is, the same processing is performed at the measurement point P2, so that weighting coefficients at channel positions of the measurement point P2 at which the same reference value (increment) is set are multiplied by the zeroth-column weighting coefficient, and the sum of the products are calculated. In other words, in the weighting coefficient array at the measurement point P2 that corresponds to the channels of each stage, the sum of the products between the first weighting coefficient and the respective remaining weighting coefficients is obtained.

[Step S12]

Sum-of-product calculation between the zeroth-column data and weighting coefficients is performed for the extracted data $I_{P1}$ and weighting coefficients $W_{P1}$ at the measurement point P1. That is, weighting coefficients at channel positions of the measurement point P1 at which the same reference value (increment) is set are multiplied by the zeroth-column data, and the sum of the products is calculated. In other words, in the data array and the weighting coefficients array at the measurement point P1 that corresponds to the channels of each stage, the sum of the products between the first data and the respective weighting coefficients is obtained. Sum-of-product calculation between the zeroth-column data and weighting coefficients is performed for the extracted data $I_{P2}$ and weighting coefficients $W_{P2}$ at the measurement point P2. That is, the same processing is performed at the measurement point P2, so that weighting coefficients at channel positions of the measurement point P2 at which the same reference value (increment) is set are multiplied by the zeroth-column data, and the sum of the products is calculated. In other words, in the data array and the weighting coefficient array at the measurement point P1 that corresponds to the channels of each stage, the sum of the products between the first data and the respective weighting coefficients is obtained.

[Step S13]

Sum-of-product calculation between the zeroth-column weighting coefficient and data is performed for the extracted weighting coefficients $W_{P1}$ and data $I_{P1}$ at the measurement point P1. That is, data at channel positions of the measurement point P1 at which the same reference value (increment) is set is multiplied by the zeroth-column weighting coefficient, and the sum of the products is calculated. In other words, in the data array and the weighting coefficient array at the measurement point P1 that corresponds to the channels of each stage, the sum of the products between the first weighting coefficient and the respective data is obtained. Sum-of-product calculation between a weighting coefficient and data is then performed for the extracted weighting coefficient $W_{P2}$ and data $I_{P2}$ at the measurement point P2. That is, the same processing is performed at the measurement point P2, so that data at channel positions of the measurement point P2 at which the same reference value (increment) is set is multiplied by the zeroth-column weighting coefficient, and the sum of the products is calculated. In other words, in the data array and the weighting coefficient array at the measurement point P2 that corresponds to the channels of each stage, the sum of the products between the first weighting coefficient and the respective data is obtained.

[Step S14]

Figure 21:
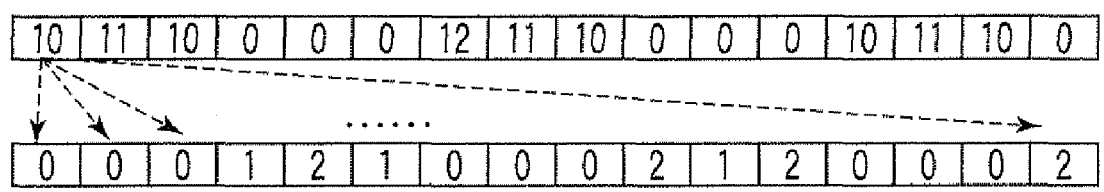
FIG. 21 is a view showing sum-of-product calculation between data at the measurement point P1 the measurement point P2.

Sum-of-product calculation between the data at the two measurement point P1 and P2 is performed for the extracted data $I_{P1}$ and $I_{P2}$ at the measurement point P1 and the measurement point P2. That is, as shown in FIG. 21, data at channel positions of the measurement point P2 at which the same reference value (increment) is set is multiplied by the zeroth-column data at the measurement point P1, and the sum of the products is calculated. In other words, in the data array at the measurement point P1 and the data array at the measurement point P2 that corresponds to the channels of each stage, the sum of the products between the first data of the data array at the measurement point P1 and the respective data of the data array at the measurement point P2 is obtained.

[Step S15]

Sum-of-product calculation between the weighting coefficients at the two measurement points P1 and P2 is performed for the extracted weighting coefficients $W_{P1}$ and $W_{P2}$ at the measurement point P1 and the measurement point P2. That is, weighting coefficients at channel positions of the measurement point P2 at which the same reference value (increment) is set are multiplied by the zeroth-column weighting coefficient at the measurement point P1, and the sum of the products is calculated. In other words, in the weighting coefficient array at the measurement point P1 and the weighting coefficients of the weighting coefficient array at the measurement point P2 that corresponds to the channels of each stage, the sum of the products between the first weighting coefficient of the weighting coefficient array at the measurement point P1 and the respective weighting coefficients of the weighting coefficient array at the measurement point P2 is obtained.

[Step S16]

Sum-of-product calculation between the zeroth-column data at the measurement point P1 and the weighting coefficients at the measurement point P2 is performed for the extracted data $I_{P1}$ at the measurement point P1 and the weighting coefficients $W_{P2}$ at the measurement point P2. That is, weighting coefficients at channel positions of the measurement point P2 at which the same reference value (increment) is set are multiplied by the zeroth-column data at the measurement point P1, and the sum of the products is calculated. In other words, in the data array at the measurement point P1 and the weighting coefficient array at the measurement point P2 that corresponds to the channels of each stage, the sum of the products between the first data of the data array at the measurement point P1 and the respective weighting coefficients of the weighting coefficient array at the measurement point P2 is obtained.

[Step S17]

Sum-of-product calculation between the zeroth-column weighting coefficient at the measurement point P1 and data at the measurement point P2 is performed for the extracted weighting coefficients $W_{P1}$ at the measurement point P1 and the extracted data $I_{P2}$ at the measurement point P2. That is, data at channel positions of the measurement point P2 at which the same reference value (increment) is set is multiplied by the zeroth-column weighting coefficient at the measurement point P1, and the sum of the products is calculated. In other words, in the data array at the measurement point P2 and the weighting coefficient array at the measurement point P1 that corresponds to the channels of each stage, the sum of the products between the first data of the data array at the measurement point P2 and the respective weighting coefficients of the weighting coefficient array at the measurement point P1 is obtained.

[Step S18]

Termination of the computation and imaging are determined. If YES, the process enters comprehensive correlation calculation. If NO, the process returns to the data acquisition in step S1.

[Step S19]

If the data read is complete (YES in step S21), auto-correlation functions for each of the two measurement points P1 and P2 and an inter-point cross-correlation function between the two measurement points P1 and P2 are estimated on the basis of the above respective calculation results. That is, correlation functions are estimated by using different analytical expressions for the respective correlation directions of P1→P2, P1→P1, and P2→P2.

For example, the data analysis unit uses the formula (S10*S11)/(S12*S13) for P1→P1 and P2→P2, and the formula (S14*S15)/(S16*S17) for P1→P2.

These analytical expressions can be expressed by $$C(\tau) = \frac{mlF_{P1}R_{P1}\text{Sum}(\tau_v) * mlW_{P1}V_{P1}\text{Sum}(\tau_v)}{mlF_{P1}V_{P1}\text{Sum}(\tau_v) * mlW_{P1}R_{P1}\text{Sum}(\tau_v)} \quad (4)$$

$$C(\tau) = \frac{mlF_{P2}R_{P2}\text{Sum}(\tau_v) * mlW_{P2}V_{P2}\text{Sum}(\tau_v)}{mlF_{P2}V_{P2}\text{Sum}(\tau_v) * mlW_{P2}R_{P2}\text{Sum}(\tau_v)} \quad (5)$$

$$C(\tau) = \frac{mlF_{P1}R_{P2}\text{Sum}(\tau_v) * mlW_{P2}V_{P2}\text{Sum}(\tau_v)}{mlF_{P1}V_{P2}\text{Sum}(\tau_v) * mlW_{P1}R_{P2}\text{Sum}(\tau_v)} \quad (6)$$

In equations (4) to (6), $mlF_PR_P\text{Sum}(\tau_v)$ represents sum-of-product calculation between data, $mlW_PV_P\text{Sum}(\tau_v)$ represents sum-of-product calculation between weighting coefficients, $mlF_PV_P\text{Sum}(\tau_v)$ represents sum-of-product calculation between the zeroth-column data and weighting coefficients, and $mlW_PR_P\text{Sum}(\tau_v)$ represents sum-of-product calculation between the zeroth-column weighting coefficient and data. Here, the subscript P is P1 or P2, and corresponds to calculation target data, i.e., data at the measurement point P1 or data at the measurement point P2. In addition, in $\tau_v = \tau_0 + \tau$, $\tau_0$ is based on a delay time $\tau_0 P$ due to the inter-point distance and a delay time $\tau_0 M$ due to the inter-point difference in measurement start time, and $\tau$ is a delay time at the time of normal correlation computation.

Equations (6) is based on cross-correlation analytical expression (7) given below.

Cross-correlation analytical expression (7) is derived by weighting the general-purpose cross-correlation function represented by equation (8). Equation (8) can be expressed as expression (9) if $N_1 = N_2 = N_{12}$ $$C(\tau) = \frac{\left(\sum D_1(t)D_2(t-\tau)\right) * \left(\sum W_1(t)W_2(t-\tau)\right)}{\left(\sum W_2(t-\tau)D_1(t)\right) * \left(\sum W_1(t)D_2(t-\tau)\right)} \quad (7)$$

$$C(\tau) = \frac{\left(\sum D_1(t)D_2(t+\tau)\right)/N_{12}}{\left((\sum D_1(t))/N_1\right) * \left((\sum D_2(t))/N_2\right)} \quad (8)$$

$$C(\tau) = \frac{\left(\sum D_1(t)D_2(t+\tau)\right) * N_{12}}{\left(\sum D_1(t)\right) * \left(\sum D_2(t)\right)} \quad (9)$$

[Step S20]

Processing such as displaying an inter-point cross-correlation function in the form of a curve is performed on the basis of each final calculation result.

As is obvious from the above description, the photometric analysis apparatus of this embodiment estimates cross-correlation functions for the two different measurement points P1 and P2. If the correlation of the analysis result on P1→P2 is high, it can be estimated that the probability of movement of the same molecule from the measurement point P1 to the measurement point P2 is high. In contrast, if the correlation is low, it can be estimated that the probability of passage of a molecule through the measurement point P2 after passage through the measurement point P1 is low, and the molecular movement frequently occurs in other directions. That is, the photometric analysis apparatus of the embodiment allows observation of the movement of a molecule between the two measurement points P1 and P2. In addition, by examining the correlativity between sets of two measurement points, molecular movement vectors are estimated.

In addition, since a calculation result is plotted for each read data, it is not necessary to wait for the completion of calculation of a large amount of data as in the conventional general-purpose scheme. It is possible to stop data read and calculation as needed and perform real-time drawing. Furthermore, it is possible to obtain the values of parameters such as the translational diffusion time of molecules and the number of molecules by logically fitting the calculation result based on the respective measurement data.

The single light applying unit intermittently scans a light beam to apply excitation light to measurement points, and the single photodetection unit detects fluorescence generated from the measurement points. That is, a single optical system is used for the measurement points. This prevents errors due to incoincidence between measurement areas, application intensities, signal transmission systems, and the like. In addition, since data at two different measurement points originate from the same measurement signal, the measurement start time error is 0. Furthermore, since only one set of hardware is required, a high-performance, low-cost optical signal analysis apparatus can be provided.

Furthermore, since only a small number of averaged data and weighting coefficients are used for the calculation of correlation functions, the time required for the calculation is short.

Although the embodiments of the present invention have been described with reference to the views of the accompanying drawing, the present invention is not limited to these embodiments. The embodiments may be variously modified and changed within the spirit and scope of the invention.

For example, the optical signal analysis apparatus according to the above embodiment detects fluorescence. However, the light to be detected is not limited to fluorescence and may be other types of light, e.g., phosphorescence, reflected light, scattered light, chemiluminescence, and bioluminescence.

The above embodiments use the correlation function analysis method. However, it suffices to use the photo counting histogram method or the coincidence analysis method instead of the above method.

In the second embodiment, the photodetection unit D time-divisionally detects light emitted from the measurement points P1, P2, . . . , Pn in the sample with the single photodetector 28. However, this unit may have photodetectors that respectively receive light emitted from the measurement points P1 and P2 in the sample.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

INDUSTRIAL APPLICABILITY

According to the present invention, there are provided an optical signal analysis apparatus and an optical signal analysis method that allow observation of the movement of a molecule between two points.

What is claimed is:

1. An optical signal analysis apparatus comprising:
   a photodetector to detect light emitted from measurement points in a sample; and
   an analyzer to analyze a molecular interaction between two of the measurement points by using fluctuation signals corresponding to fluctuations of the light from the measurement points that are detected by the photodetector, the analyzer calculating sum of data and sum of products between data, counting the number of times of sum-of-product calculation at each of the measurement points, and performing auto-correlation calculation and inter-point cross-correlation calculation based on the calculation results for each of the measurement points;
   wherein the analyzer divides a time-serially measured data obtained by repeatedly measuring two of the measurement points into a data table and a weighting coefficient table at each measurement point, sets a calculation channel for data and weighting coefficient based on an octave method and analyzes a movement vector of a molecule between two points by estimating at least an inter-point cross-correlation.

2. An optical signal analysis apparatus according to claim 1, wherein light detected by the photodetector is one of fluorescence, phosphorescence, reflected light, scattered light, chemiluminescence, and bioluminescence.

3. An optical signal analysis apparatus according to claim 1, further comprising an excitation light applier to apply excitation light to the measurement points.

4. An optical signal analysis apparatus according to claim 3, wherein the excitation light applier includes light applying units that continuously apply excitation light to the measurement points.

5. An optical signal analysis apparatus according to claim 3, wherein the excitation light applier comprises a single light applying unit.

6. An optical signal analysis apparatus according to claim 5, wherein the light applying unit time divisionally applies excitation light to the measurement points.

7. An optical signal analysis apparatus according to claim 5, wherein the analyzer generates pseudo signals or pseudo data respectively corresponding to the light from the measurement points on the basis of the fluctuation signals detected by the photodetector.

8. An optical signal analysis apparatus according to claim 7, wherein the analyzer interpolates the pseudo signal or pseudo data by using a signal or data having a predetermined value in a period during which a signal or data is omitted due to the time divisional detection.

9. An optical signal analysis apparatus according to claim 7, wherein the analyzer estimates a cross correlation function between two of the pseudo signals or pseudo data.

10. An optical signal analysis apparatus according to claim 9, wherein the analyzer further includes an influence preventer to prevent an influence of a period during which a signal or data is omitted due to the time divisional detection on an analysis result when estimating the cross correlation function.

11. An optical signal analysis apparatus according to claim 10, wherein the influence preventer assigns different weights between a period during which a signal or data is omitted due to the time divisional detection and another period.

12. An optical signal analysis apparatus according to any one of claims 1 to 3, wherein the photodetector includes photodetection units that respectively receive light emitted from the measurement points.

13. An optical signal analysis apparatus according to claim 12, wherein the analyzer estimates a cross correlation function on the basis of the two fluctuation signals at the two measurement points.

14. An optical signal analysis apparatus according to any one of claims 1 to 3, wherein the photodetector comprises a single photodetection unit.

15. An optical signal analysis apparatus according to claim 14, wherein the photodetection unit time divisionally detects the light from the measurement points.

16. An optical signal analysis method comprising:
   a photodetection step of detecting light emitted from measurement points in a sample; and
   an analysis step of analyzing a molecular interaction between two of the measurement points by using fluctuation signals corresponding to fluctuations of the light from the measurement points, the analysis step calculating sum of data and sum of products between data, counting the number of times of sum-of-product calculation at each of the measurement points, and performing auto-correlation calculation and inter-point cross-correlation calculation based on the calculation results for each of the measurement points wherein the analysis step comprises dividing a time-serially measured data obtained by repeatedly measuring two of the measurement points into a data table and weighting coefficient table at each measurement point, setting a calculation channel for data and weighting coefficient based on an octave method, and analyzing a movement vector of a molecule between two points by estimating at least an inter-point cross-correlation.

17. An optical signal analysis method according to claim 16, wherein the light detected in the photodetection step is one of fluorescence, phosphorescence, reflected light, scattered light, chemiluminescence, and bioluminescence.

18. An optical signal analysis method according to claim 16, further comprising an excitation light applying step of applying excitation light to the measurement points.

19. An optical signal analysis method according to claim 18, wherein in the excitation light applying step, excitation light is continuously applied to the measurement points.

20. An optical signal analysis method according to claim 18, wherein in the excitation light applying step, excitation light is time divisionally applied to the measurement points.

21. An optical signal analysis method according to claim 18, wherein in the photodetection step, the light from the measurement points is time divisionally detected.

22. An optical signal analysis method according to any one of claims 20 and 21, wherein in the analysis step, pseudo signals or pseudo data respectively corresponding to the light from the measurement points are generated on the basis of the fluctuation signals.

23. An optical signal analysis method according to claim 22, wherein in the analysis step, the pseudo signal or pseudo data is interpolated by using a signal or data having a predetermined value in a period during which a signal or data is omitted due to the time divisional detection.

24. An optical signal analysis method according to claim 22, wherein in the analysis step, a cross correlation function between two of the pseudo signals or pseudo data is estimated.

25. An optical signal analysis method according to claim 24, wherein the analysis step further includes an influence prevention step of preventing an influence of a period during which a signal or data is omitted due to the time divisional detection on an analysis result when estimating the cross-correlation function.

26. An optical signal analysis method according to claim 25, wherein the influence prevention step assigns different weights between a period during which a signal or data is omitted due to the time divisional detection and another period.

27. An optical signal analysis method according to any one of claims 16 to 18, wherein in the photodetection step, light emitted from the measurement points is respectively detected by photodetection units.

28. An optical signal analysis method according to claim 27, wherein the analysis step estimates a cross correlation function on the basis of two fluctuation signals corresponding to the two measurement points.

* * * * *